(12) United States Patent
Diolaiti

(10) Patent No.: US 12,005,574 B2
(45) Date of Patent: Jun. 11, 2024

(54) SYSTEMS AND METHODS FOR MOTION CONTROL OF STEERABLE DEVICES

(71) Applicant: Intuitive Surgical Operations, Inc., Sunnyvale, CA (US)

(72) Inventor: Nicola Diolaiti, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 638 days.

(21) Appl. No.: 17/279,818

(22) PCT Filed: Oct. 1, 2019

(86) PCT No.: PCT/US2019/054016
§ 371 (c)(1),
(2) Date: Mar. 25, 2021

(87) PCT Pub. No.: WO2020/072460
PCT Pub. Date: Apr. 9, 2020

(65) Prior Publication Data
US 2022/0009085 A1     Jan. 13, 2022

Related U.S. Application Data

(60) Provisional application No. 62/741,354, filed on Oct. 4, 2018.

(51) Int. Cl.
*B25J 9/10*     (2006.01)
*A61B 34/35*    (2016.01)
(Continued)

(52) U.S. Cl.
CPC .............. *B25J 9/065* (2013.01); *A61B 34/35* (2016.02); *A61B 34/37* (2016.02);
(Continued)

(58) Field of Classification Search
CPC ... B25J 9/065; B25J 9/10; B25J 9/1005; B25J 9/1633; B25J 13/089; B25J 15/02;
(Continued)

(56) References Cited

U.S. PATENT DOCUMENTS 5,704,791 A * 1/1998 Gillio ................... G09B 5/14
                                                600/101
5,768,122 A * 6/1998 Motoc .................. G05B 19/416
                                                706/900
(Continued)

FOREIGN PATENT DOCUMENTS

EP          2470089 A1     7/2012
WO     WO-2016191298 A1    12/2016
(Continued)

OTHER PUBLICATIONS

International Preliminary Report on Patentability for Application No. PCT/US2019/054016, dated Apr. 15, 2021, 09 pages.
(Continued)

*Primary Examiner* — Manglesh M Patel
(74) *Attorney, Agent, or Firm* — Haynes & Boone, LLP

(57) ABSTRACT

A system may comprise a control device configured to receive user inputs and a manipulator system including an actuator configured to receive and drive a steerable device. The system may also comprise a control system communicatively coupled to the manipulator system. The control system may be configured to track a virtual user-instructed position based on a first user input, determine a device position of a portion of the steerable device, and determine a position discrepancy in a first direction between the determined device position and the virtual user-instructed position. The control system may also be configured to receive a second user input commanding motion of the steerable device in a second direction, opposite the first direction. In response to the second user input, the position (Continued)

discrepancy may be reduced based on an aspect of the second user input and a catch-up profile.

20 Claims, 5 Drawing Sheets

(51) Int. Cl.
*A61B 34/37* (2016.01)
*B25J 9/06* (2006.01)
*B25J 13/08* (2006.01)
*B25J 15/02* (2006.01)
*G05B 19/4155* (2006.01)
*A61B 34/30* (2016.01)

(52) U.S. Cl.
CPC .... *G05B 19/4155* (2013.01); *A61B 2034/301* (2016.02); *G05B 2219/50391* (2013.01)

(58) Field of Classification Search
CPC ... A61B 34/35; A61B 34/37; A61B 2034/301; G05B 19/4155; G05B 2219/50391; G05D 1/43
USPC ................................. 700/257, 254
See application file for complete search history.

(56) References Cited

U.S. PATENT DOCUMENTS

| | | | | |
|---|---|---|---|---|
| 5,855,553 A * | 1/1999 | Tajima | ................... | A61B 34/70 600/407 |
| 6,223,100 B1 * | 4/2001 | Green | ................... | H04N 13/296 348/E13.016 |
| 6,233,504 B1 * | 5/2001 | Das | ................... | G06F 3/016 600/595 |
| 6,380,732 B1 | 4/2002 | Gilboa | | |
| 6,389,187 B1 | 5/2002 | Greenaway et al. | | |
| 6,728,599 B2 * | 4/2004 | Wang | ................... | A61B 34/70 600/595 |
| 6,772,053 B2 * | 8/2004 | Niemeyer | .......... | A61B 1/00149 348/E13.016 |
| 6,804,581 B2 * | 10/2004 | Wang | ................... | A61B 34/70 600/101 |
| 6,839,612 B2 * | 1/2005 | Sanchez | ................. | A61B 34/35 606/1 |
| 7,248,944 B2 * | 7/2007 | Green | ................... | A61B 34/70 348/E13.059 |
| 7,316,681 B2 | 1/2008 | Madhani et al. | | |
| 7,772,541 B2 | 8/2010 | Froggatt et al. | | |
| 8,489,235 B2 * | 7/2013 | Moll | ....................... | A61B 34/37 700/1 |
| 8,918,211 B2 * | 12/2014 | Diolaiti | ................. | A61B 34/37 901/33 |
| 9,259,274 B2 | 2/2016 | Prisco | | |
| 9,452,276 B2 | 9/2016 | Duindam et al. | | |
| 9,931,025 B1 | 4/2018 | Graetzel et al. | | |
| 10,618,161 B2 * | 4/2020 | Watanabe | ................. | B25J 9/10 |
| 11,116,581 B2 * | 9/2021 | Duindam | ............... | A61B 34/35 |
| 11,638,999 B2 * | 5/2023 | Itkowitz | ................. | B25J 9/1671 606/1 |
| 11,666,400 B2 * | 6/2023 | Griffiths | ................. | A61B 46/10 606/130 |
| 11,672,622 B2 * | 6/2023 | Johnson | ................. | A61B 34/30 700/245 |
| 11,707,336 B2 * | 7/2023 | Itkowitz | ................. | B25J 9/1612 606/130 |
| 2006/0013523 A1 | 1/2006 | Childers et al. | | |
| 2009/0024142 A1 * | 1/2009 | Ruiz Morales | ........ | A61B 34/37 606/130 |
| 2010/0168763 A1 * | 7/2010 | Zhao | ....................... | A61B 34/20 606/130 |
| 2010/0198402 A1 * | 8/2010 | Greer | ......................... | B25J 3/04 901/41 |
| 2011/0071543 A1 | 3/2011 | Prisco et al. | | |
| 2011/0306873 A1 * | 12/2011 | Shenai | ................. | A61B 8/0841 600/424 |
| 2014/0330432 A1 * | 11/2014 | Simaan | ................... | B25J 9/1625 700/250 |
| 2015/0011830 A1 | 1/2015 | Hunter et al. | | |
| 2015/0045812 A1 * | 2/2015 | Seo | ......................... | A61B 34/30 606/130 |
| 2015/0314440 A1 * | 11/2015 | Parker | .................... | B25J 9/1612 700/253 |
| 2016/0228203 A1 | 8/2016 | Yamanaka et al. | | |
| 2018/0221101 A1 | 8/2018 | Prisco et al. | | |
| 2020/0253669 A1 * | 8/2020 | Diolaiti | ............ | A61B 17/00234 |
| 2021/0393349 A1 * | 12/2021 | Diolaiti | .................. | A61B 34/37 |

FOREIGN PATENT DOCUMENTS

| | | | | |
|---|---|---|---|---|
| WO | WO-2018005928 A1 * | 1/2018 | ......... | A61B 1/00006 |
| WO | WO-2019074786 A1 * | 4/2019 | ............ | A61B 1/005 |

OTHER PUBLICATIONS

International Search Report and Written Opinion for Application No. PCT/US2019/054016, dated May 8, 2019, 16 pages (ISRG12640/PCT).

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR MOTION CONTROL OF STEERABLE DEVICES

CROSS-REFERENCE TO RELATED APPLICATIONS

This application is the U.S. national phase of International Application No. PCT/US2019/054016, filed Oct. 1, 2019, which designates the U.S. and claims priority to and the benefit of U.S. Provisional Application 62/741,354 filed Oct. 4, 2018, both of which are incorporated by reference herein in their entirety.

FIELD

Examples described herein relate to systems and methods for a procedure, such as systems and methods for controlling steerable devices of systems.

BACKGROUND

Instruments can be used to manipulate and perform tasks in a work space. Such instruments may be configured to be supported and operated partially or entirely by manipulator assemblies. Such instruments and manipulator assemblies can be used to perform non-medical procedures or medical procedures. For example, medical tools or medical manipulators can be used to perform minimally invasive medical procedures. As another example, industrial tools or industrial manipulators can be used in manufacture or testing. As yet other examples, tools or manipulators can be used in procedures for entertainment, exploration, and various other purposes.

Minimally invasive medical techniques may generally be intended to reduce the amount of tissue that is damaged during invasive medical procedures, thereby reducing patient recovery time, discomfort, and harmful side effects. Such minimally invasive techniques may be performed through natural orifices in a patient anatomy or through one or more incisions. Through these natural orifices or incisions, clinicians may insert, medical tools to reach a target tissue location. Minimally invasive medical tools include instruments such as therapeutic instruments, diagnostic instruments, and surgical instruments. Minimally invasive medical tools may also include imaging instruments such as endoscopic instruments that provide a user with a field of view within the patient anatomy.

Some medical and non-medical instruments (including manipulation instruments, imaging instruments or other sensing instruments, etc.) may be teleoperated or otherwise computer-assisted. It would be advantageous to provide intuitive controls for operating these instruments and other steerable devices and for the controls to respond quickly and accurately to user input during a procedure.

SUMMARY

The following presents a simplified summary of various examples described herein and is not intended to identify key or critical elements or to delineate the scope of the claims.

In one example, a system may include a control device configured to receive user inputs, a manipulator system including an actuator configured to receive and drive a steerable device, and a control system communicatively coupled to the manipulator system and the control device. The control system may be configured to track a virtual user-instructed position based on a first user input, determine a device position of a portion of the steerable device, and determine a position discrepancy in a first direction between the determined device position and the virtual user-instructed position. The control system may also be configured to receive a second user input commanding motion of the steerable device in a second direction. At least a portion of the second direction is opposite the first direction. In response to the second user input, the control system is configured to reduce the position discrepancy based on an aspect of the second user input and a catch-up profile.

In another example, a method may include receiving, from a master controller, a first user input indicating a movement of a steerable elongate device in a first direction of motion and tracking a virtual user-instructed position based on the first user input. The method may also include controlling motion of the steerable elongate device based on the first user input and detecting, from a sensor of the steerable elongate device, a current device position of the steerable elongate device. The method may also include determining a position discrepancy between the detected current device position and the virtual user-instructed position and receiving a second user input from the master controller in a second direction of motion. At least a portion of the position of the second direction is opposite the first direction of motion. In response to the second user input, the position discrepancy may be reduced based on a catch-up profile.

In another example, an apparatus may include one or more processors and non-transitory computer memory storing machine-executable instructions. When executed by the one or more processors, the machine-executable instructions may cause the apparatus to receive, from a control device, a first user input commanding motion of a steerable device in a first direction and track a virtual user-instructed position based on the first user input. When executed by the one or more processors, the machine-executable instructions may also cause the apparatus to command an actuator coupled to the steerable device to move the steerable device in the first direction based on the first user input. Movement of the steerable device in response to the first user input may generate a position discrepancy. When executed by the one or more processors, the machine-executable instructions may also cause the apparatus to detect, from a sensor of the steerable device, a device position of a portion of the steerable device and determine a measure of the position discrepancy. When executed by the one or more processors, the machine-executable instructions may also cause the apparatus to receive, from the control device, a second user input commanding motion of the steerable device in a second direction. At least a portion of the second direction may be opposite the first direction. In response to the second user input, the position discrepancy may be reduced based on an aspect of the second user input and a catch-up profile.

It is to be understood that both the foregoing general description and the following detailed description are illustrative and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1:
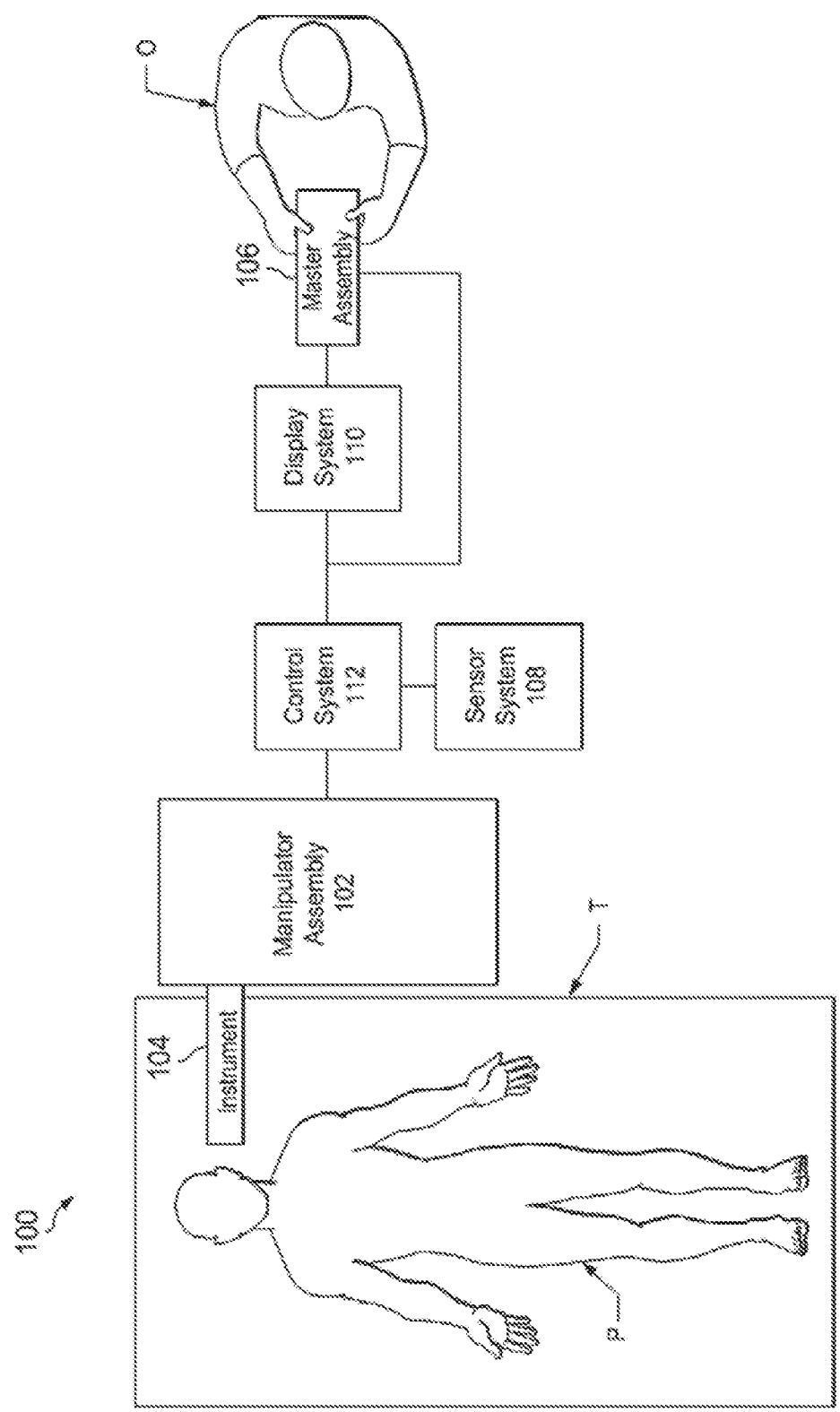
FIG. 1 is a simplified diagram of a medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The technology described herein provides a technique for controlling a steerable device such as an instrument of a robotic device or system. Examples of applicable robotic devices or systems include medical devices, teleoperated or otherwise operated, that drive a flexible elongate device into a passageway such as an airway or a vessel. As an illustrative and enabling example, various aspects of the disclosed technology are described with respect to an example flexible robotic device or system, such as a robotically controlled catheter described with respect to FIGS. 1, 2A, and 2B. In various embodiments, a user instructs the system to drive the robotically controlled catheter using actuators of the system. When the force imparted by the actuators is opposed, tension may accumulate within the catheter. The disclosed technology for controlling the catheter or other instrument described with respect to FIGS. 3-8 can be implemented to control the manner in which tension is generated and released to provide an intuitive control technique with a number of advantages including smooth changes in tension and a high degree of responsiveness to user input.

FIG. 1 is a simplified diagram of a robotic medical system 100 according to some embodiments. In some embodiments, medical system 100 may be suitable for use in, for example, surgical, diagnostic, therapeutic, or biopsy procedures. While some embodiments are provided herein with respect to such procedures, any reference to medical or surgical instruments and medical or surgical methods is non-limiting. The systems, instruments, and methods described herein may be used in robotic systems for animals, human cadavers, animal cadavers, portions of human or animal anatomy, non-surgical diagnosis, as well as for industrial systems and/or other general robotic systems.

As shown in FIG. 1, medical system 100 may include a manipulator assembly 102 for operating a medical instrument 104 in performing various procedures on a patient P. Medical instrument 104 may extend into an internal site within the body of patient P via an opening in the body of patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 may be mounted to and/or positioned near an operating table T. A master assembly 106 allows an operator O (e.g., a surgeon, a clinician, or a physician as illustrated in FIG. 1) to view the interventional site and to control manipulator assembly 102.

Master assembly 106 may be located at an operator console which is may be located in the same room as operating table T, such as at the side of a surgical table on which patient P is located. However, it should be understood that operator O can be located in a different room or a completely different building from patient P. Master assembly 106 generally includes one or more control devices for controlling manipulator assembly 102. The control devices may include any number of a variety of input devices, such as joysticks, trackballs, scroll wheels, directional pads, buttons, data gloves, trigger-guns, hand-operated controllers, voice recognition devices, body motion or presence sensors, and/or the like.

Manipulator assembly 102 supports medical instrument 104 and may include: kinematic structure of one or more non-servo controlled links (e.g., one or more links that may be manually positioned and locked in place, generally referred to as a set-up structure), one or more servo controlled links (e.g., one or more links that may be controlled in response to commands from the control system), and/or a manipulator. Manipulator assembly 102 may include a plurality of actuators or motors that drive inputs on medical instrument 104 in response to commands from the control system (e.g., a control system 112). The actuators may include drive systems that when coupled to medical instrument 104 may advance medical instrument 104 into a naturally or surgically created anatomic orifice. Other drive systems may move the distal portion of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like.

Medical system 100 may include a sensor system 108 with one or more sub-systems for receiving information about the manipulator assembly 102 and/or the medical instrument 104. Such sub-systems may include a position/location sensor system (e.g., an electromagnetic (EM) sensor system); a shape sensor system for determining the position, orientation, speed, velocity, pose, and/or shape of a distal portion and/or of one or more segments along a flexible body that may make up medical instrument 104; a visualization system for capturing images from the distal portion of medical instrument 104; and/or actuator position sensors such as resolvers, encoders, potentiometers, and the like that describe the rotation and orientation of the motors controlling the instrument 104.

Medical system 100 may include a display system 110 for displaying an image or representation of the surgical site and medical instrument 104. In some examples, display system 110 may present pre-operative or intra-operative images of a surgical site using image modalities such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. In some embodiments, medical instrument 104 may include a visualization system that includes an image capture assembly to record a concurrent or real-time image of a surgical site and to provide the image to the operator O through one or more displays of display system 110.

In some examples, medical system 100 may configure the displayed representations, the medical instrument 104, and the controls of master assembly 106 such that the relative positions of the medical instruments are similar to the relative positions of the eyes and/or hands of operator O. In this manner, operator O can manipulate medical instrument 104 and hand controls as if viewing the workspace in substantially true presence.

In some examples, such as for purposes of image-guided medical procedures, display system 110 may display a virtual navigational image in which the actual location of medical instrument 104 is registered (e.g., dynamically referenced) with the preoperative or concurrent images/model. This may be done to present the operator O with a virtual image of the internal surgical site from a viewpoint of medical instrument 104.

Medical system 100 may also include control system 112. Control system 112 includes at least one memory and at least one computer processor (not shown) for effecting control between manipulator assembly 102, medical instrument 104, master assembly 106, sensor system 108, and/or display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to manipulator assembly 102, another portion of the processing being performed at master assembly 106, and/or the like. The processors of control system 112 may execute instructions corresponding to processes disclosed herein and described in more detail below.

In some examples, control system 112 may receive force and/or torque feedback from medical instrument 104. Responsive to the feedback, control system 112 may transmit signals to master assembly 106. In some examples, control system 112 may transmit signals instructing one or more actuators of manipulator assembly 102 to move medical instrument 104.

Control system 112 may obtain sensor data from sensor system 108 that is used to compute an approximate location of medical instrument 104 with respect to the anatomy of patient P. The system may implement the sensor system 108 to register and display the medical instrument together with preoperatively or intraoperatively recorded medical images. For example, PCT Publication WO 2016/191298 (published Dec. 1, 2016 and titled "Systems and Methods of Registration for Image Guided Surgery"), which is incorporated by reference herein in its entirety, discloses example systems.

Medical system 100 may further include operations and support systems such as illumination systems, articulation (e.g., steering) control systems, irrigation systems, and/or suction systems (not shown). In some embodiments, medical system 100 may include more than one manipulator assembly and/or more than one master assembly. The exact number of manipulator assemblies may depend on the medical procedure and space constraints within the operating room, among other factors. Master assembly 106 may be co-located or they may be positioned in separate locations. Multiple master assemblies may allow more than one operator to control one or more manipulator assemblies in various combinations.

Figure 2A:
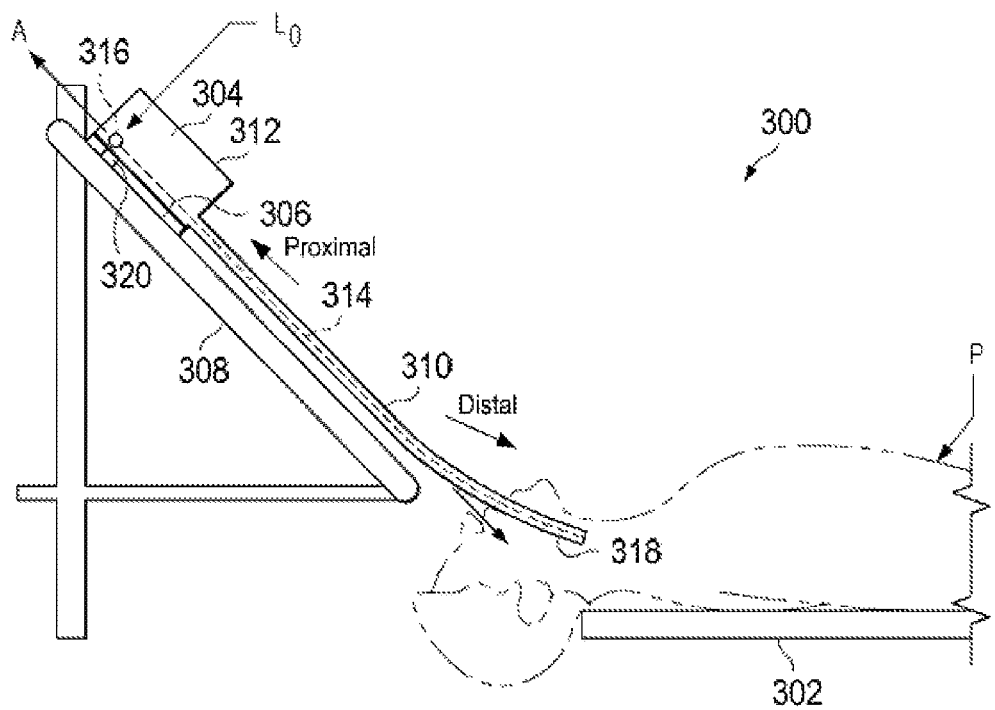
FIGS. 2A and 2B are simplified diagrams of side views of a patient coordinate space including a medical instrument mounted on an insertion assembly according to some embodiments.
Figure 2B:
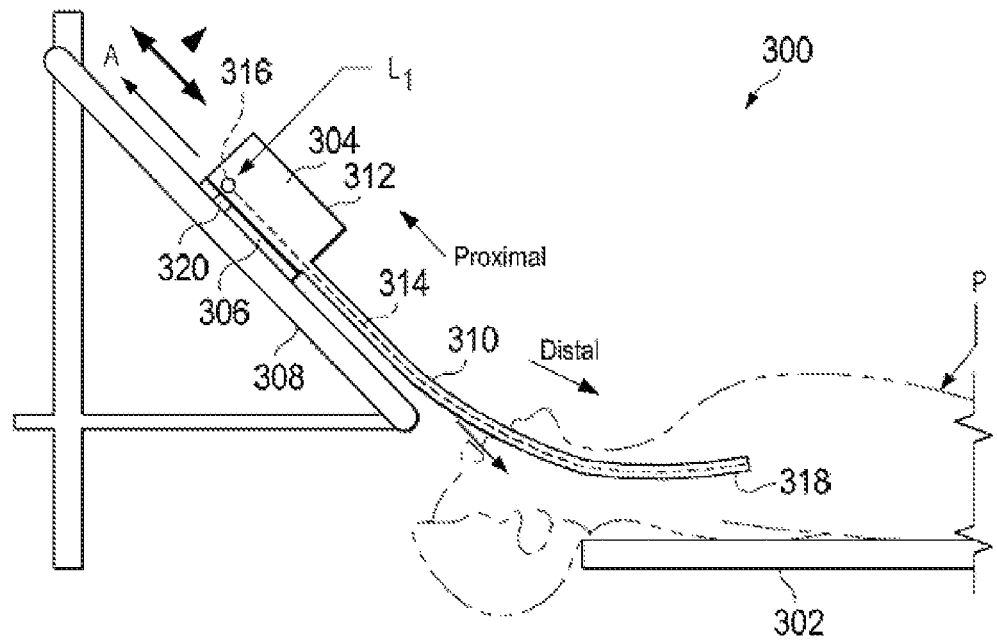

FIGS. 2A and 2B are simplified diagrams of side views of a patient coordinate space including a medical instrument mounted on an insertion assembly according to some embodiments. As shown in FIGS. 2A and 2B, a surgical environment 300 may include a patient P positioned on a table T. Patient P may be stationary within the surgical environment 300 in the sense that gross patient movement is limited by sedation, restraint, and/or other means. Cyclic anatomic motion including respiration and cardiac motion of patient P may continue. Within surgical environment 300, a medical instrument 304 is used to perform a medical procedure which may include, for example, surgery, biopsy, ablation, illumination, irrigation, suction a system registration procedure. The medical instrument 304 may be, for example, the instrument 104. The instrument 304 includes a flexible elongate device 310 (e.g., a catheter) coupled to an instrument body 312. Elongate device 310 includes one or more channels (not shown) sized and shaped to receive a medical tool (not shown).

Elongate device 310 may also include one or more sensors (e.g., components of the sensor system 108). In some examples, an articulation sensor 314, such as a fiber optic shape sensor, may be fixed at a proximal point 316 on instrument body 312. The proximal point 316 of the articulation sensor 314 may be movable with instrument body 312, and the location of the proximal point 316 may be known (e.g., via a tracking sensor or other tracking device). Articulation sensor 314 may measure a shape from the proximal point 316 to another point, such as distal portion 318 of the elongate device 310. Articulation sensor 314 may be aligned with the flexible elongate device 310 (e.g., provided within an interior channel (not shown) or mounted externally). In some examples, the optical fiber may have a diameter of approximately 200 μm. In other examples, the diameter may be larger or smaller. The articulation sensor 314 may be used to determine the shape of flexible elongate device 310. Optical fibers including Fiber Bragg Gratings (FBGs) may be used to provide strain measurements in structures in one or more dimensions. Various systems and methods for monitoring the shape and relative position of an optical fiber in three dimensions are described in U.S. patent application Ser. No. 11/180,389 (filed Jul. 13, 2005 and titled "Fiber optic position and shape sensing device and method relating thereto"); U.S. patent application Ser. No. 12/047,056 (filed on Jul. 16, 2004 and titled "Fiber-optic shape and relative position sensing"); and U.S. Pat. No. 6,389,187 (filed on Jun. 17, 1998 and titled "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. Various systems for using fiber optic sensors to register and display a surgical instrument with surgical images are provided in PCT Publication WO 2016/191298 (published Dec. 1, 2016 and titled "Systems and Methods of Registration for Image Guided Surgery"), which is incorporated by reference herein in its entirety.

In some examples, position sensors such as electromagnetic (EM) sensors, may be incorporated into the medical instrument 304. A series of position sensors may be positioned along the flexible elongate device 310 and used for shape sensing. In some examples, position sensors may be configured and positioned to measure six degrees of freedom, e.g., three position coordinates X, Y, Z and three orientation angles indicating pitch, yaw, and roll of a base point. In some examples, position sensors may be configured and positioned to measure five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999 and titled "Six-Degree of Freedom Tracking System Having a Passive Transponder on the Object Being Tracked"), which is incorporated by reference herein in its entirety.

Elongate device 310 may house cables, linkages, or other steering controls (not shown) that extend between instrument body 312 and distal portion 318 to controllably bend distal portion 318. In some examples, at least four cables are used to provide independent up-down steering to control a pitch of distal portion 318 and left-right steering to control a yaw of distal portion 318. Steerable elongate devices are described in detail in U.S. patent application Ser. No. 13/274,208 (filed Oct. 14, 2011) (disclosing "Catheter with Removable Vision Probe"), which is incorporated by reference herein in its entirety. The instrument body 312 may include drive inputs that removably couple to and receive power from drive elements, such as actuators, of the assembly.

Instrument body 312 may be coupled to instrument carriage 306. Instrument carriage 306 may be mounted to an insertion stage 308 fixed within the surgical environment 300. Alternatively, insertion stage 308 may be movable but have a known location (e.g., via a tracking sensor or other tracking device) within surgical environment 300. Instrument carriage 306 may be a component of a manipulator assembly (e.g., manipulator assembly 102) that couples to medical instrument 304 to control insertion motion (e.g., motion along the A axis) and/or motion of the distal portion 318 of the elongate device 310 in multiple directions such as yaw, pitch, and/or roll. Instrument carriage 306 or insertion stage 308 may include actuators, such as servomotors, (not shown) that control motion of instrument carriage 306 along insertion stage 308.

A sensor device 320, which may be a component of the sensor system 108 may provide information about the position of instrument body 312 as it moves on insertion stage 308 along an insertion axis A. Sensor device 320 may include one or more resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 2A shows the instrument body 312 and the instrument carriage 306 in a retracted position along insertion stage 308. In this retracted position, the proximal point 316 is at a position $L_0$ on axis A. In FIG. 2B, instrument body 312 and instrument carriage 306 have advanced along the linear track of insertion stage 308, and the distal portion 318 of elongate device 310 has advanced into patient P. In this advanced position, the proximal point 316 is at a position $L_0$ on the axis A. In some examples, encoder and/or other position data from one or more actuators controlling movement of instrument carriage 306 along insertion stage 308 and/or one or more position sensors associated with instrument carriage 306 and/or insertion stage 308 may be used to determine the position of proximal point 316 relative to position $L_0$. In some examples, this position may further be used as an indicator of the distance or insertion depth to which distal portion 318 of elongate device 310 is inserted into the passageway(s) of the anatomy of patient P.

Figure 3:
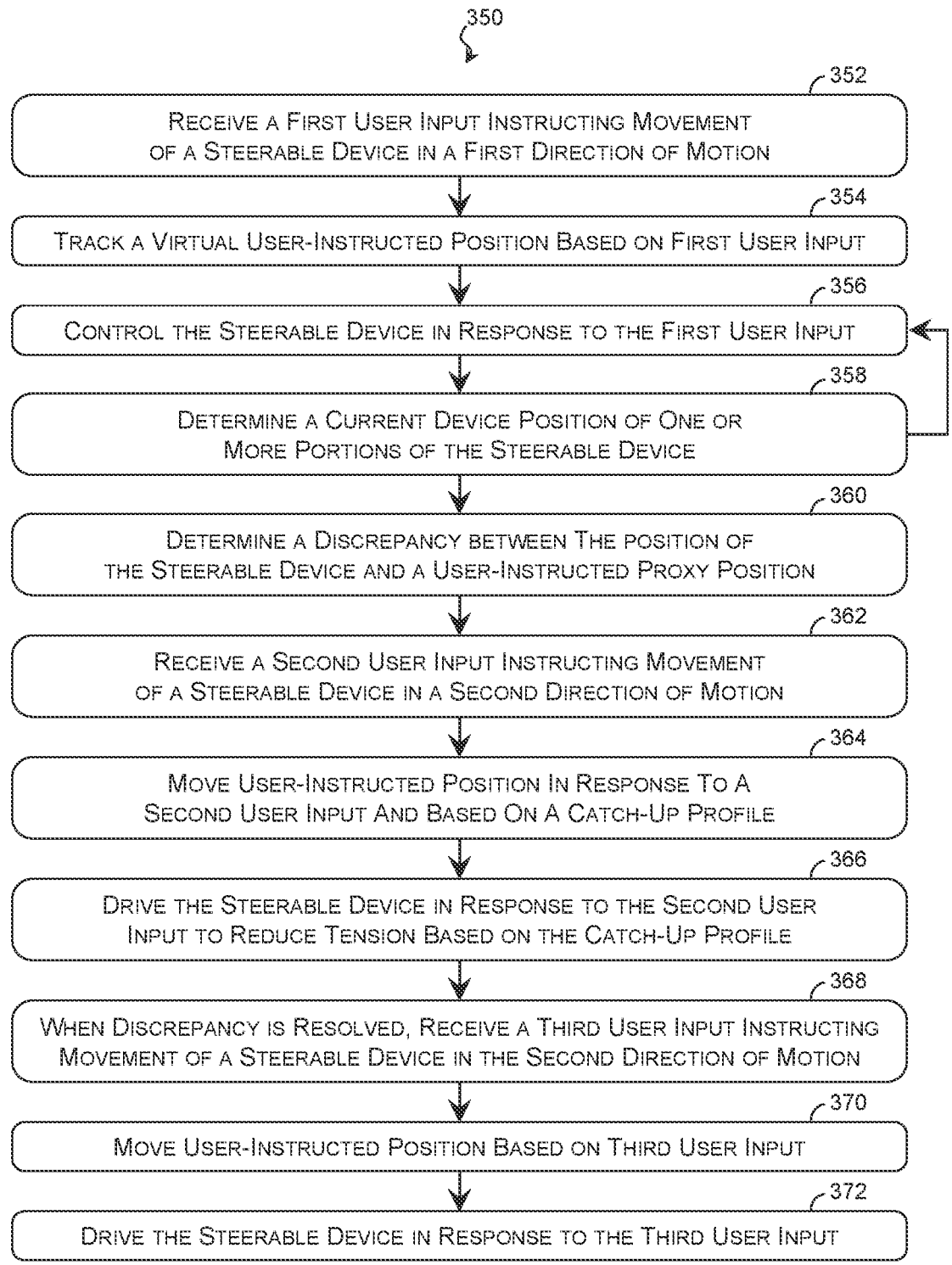
FIG. 3 is a flowchart illustrating a method of controlling a steerable device according to some embodiments.
Figure 4:
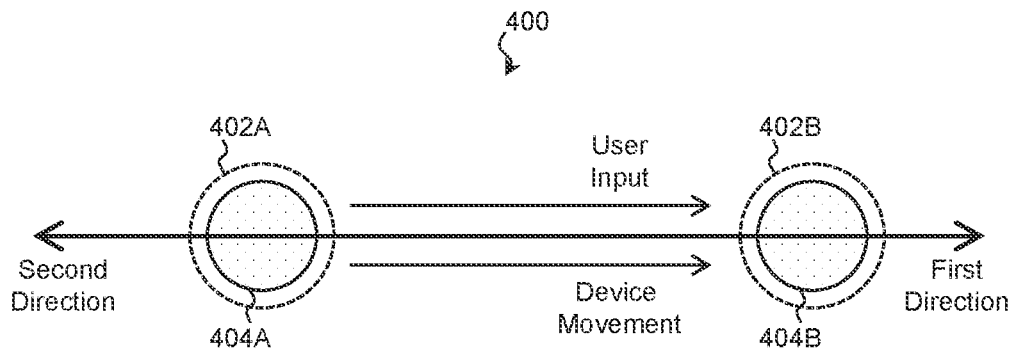
FIGS. 4-6 are diagrams illustrating relationships between user inputs and positions of a steerable device according to some embodiments.
Figure 5:
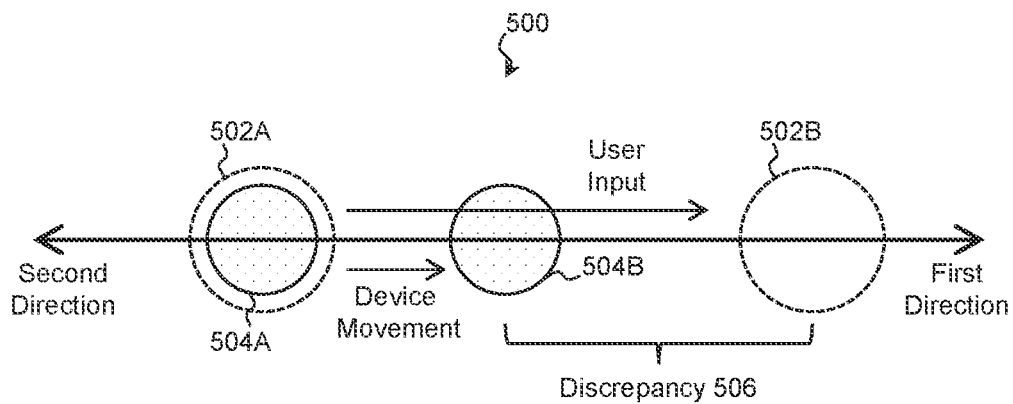
Figure 6:
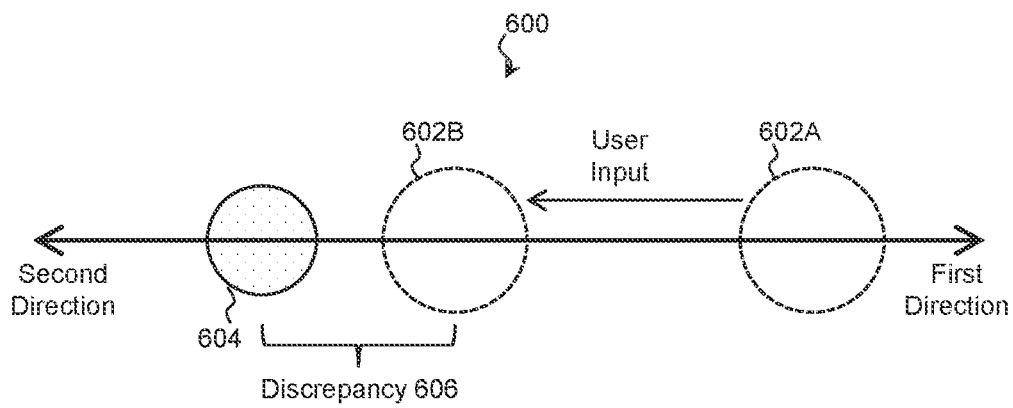

A method for controlling a steerable device—such as the flexible elongate device 310 and/or instrument 104 described above—is described with reference to FIGS. 3-7C. FIG. 3 is a flowchart describing a method 350 of controlling a steerable device according to some embodiments. The method 350 is illustrated in FIG. 3 as a set of operations or processes. The processes illustrated in FIG. 3 may be performed in a different order than the order shown in FIG. 3, and one or more of the illustrated processes might not be performed in some embodiments of method 350. Additionally, one or more processes that are not expressly illustrated in FIG. 3 may be included before, after, in between, or as part of the illustrated processes. In some embodiments, one or more of the processes of method 350 may be implemented, at least in part, in the form of executable code stored on non-transitory, tangible, machine-readable media that, when run by one or more processors (e.g., the processors of the control system 112 above), may cause the one or more processors to perform one or more of the processes. FIGS. 4-6 are diagrams illustrating relationships between user inputs and positions of the steerable device in control environments according to some embodiments.

Referring to process 352 of FIG. 3, a system, such as the medical system 100 above, may receive a first user input that instructs the system to move a steerable device of the system in a first direction of motion. The first direction of motion may be along any axis (e.g., the insertion axis, either or both of the lateral axes, etc.) or may be in any orientation (e.g., yaw, pitch, roll, etc.). The user input may be provided by an operator O using a control device of a master assembly 106, and in various examples, the control devices may include a joystick, a trackball, a scroll wheel, a directional pad, a button, a data glove, a trigger-gun, a hand-operated controller, a voice recognition device, a body motion or presence sensor, and/or other suitable control device. The user input may include a desired velocity, a desired position, and/or other instructions for the steerable device.

Referring to process 354 of FIG. 3 and to FIG. 4, the system may track a user-instructed position associated with the steerable device in response to the first user input. In the control environment 400 of FIG. 4, user-instructed positions, which may be referred to as the master or proxy positions, are represented by circles 402A and 402B. The user-instructed position may be a virtual position in that it may vary from the actual position of the steerable device. At cycle zero where teleoperation is initiated, the user-instructed position (e.g., position 402A) may match the position of the steerable device (e.g., position 404A). In the illustrated examples, the first user input may instruct the system to drive the steerable device such that a portion of the steerable device (e.g., a distal portion of the steerable device) moves from position 402A to position 402B. The system may track the movement of the user-instructed position from position 402A to position 402B as shown.

In examples where the first user input includes a measure of velocity, the amount that the user-instructed position is moved may be determined by applying any applicable velocity modification, such as a positional limit or a catch-up modification described in more detail below in the context of a second user input. The modified velocity may then be integrated (e.g., multiplied by the cycle time for a velocity of constant magnitude) to determine the amount to move the user-instructed position.

Referring to process 356 of FIG. 3, the system may control the steerable device in response to the first user input. In some embodiments, the control system 112 of the medical system 100 may cause actuators of the manipulator assembly 102 to apply force to cables, linkages, pull wires, tendons, or other steering controls within the steerable device in response to the first user input. In some embodiments, the control system 112 of the medical system may cause actuators of an insertion stage (e.g., insertion stage 308) to apply force to the steerable device in response to the first user input. The user input may be translated into an actuator position and/or an amount of force applied by an actuator.

Referring to process 358, the system may determine the current position of one or more portions of the steerable device in response to the movement of the actuators in process 356. For example, the control system 112 may receive data from sensors of the sensor system 108 (e.g., shape sensors of the steerable device, position sensors, actuator position sensors, etc.), and may utilize the received data to determine the position, orientation, speed, velocity, pose, and/or shape of one or more segments along the steerable device. For example, the control system 112 may utilize the received data to determine the position, orientation, speed, velocity, pose, and/or shape of a distal portion of the steerable device or another portion of the steerable device. The control system 112 may also consider historical pose data to reconstruct the shape of the steerable device over an interval of time. In some embodiments, the control system 112 may receive data from sensors of the sensor system 108 associated with movement of instrument carriage 306 along insertion stage 308 and may utilize the received data to determine the position, orientation, speed, velocity, pose, and/or shape of one or more segments along the steerable device. The position of the steerable device determined in process 358 may be fed back to process 356 in a feedback loop to adjust the actuators so that the steerable device properly responds to the user input of process 352. For example, the actuators may be controlled such that, when the steerable device is unopposed, the position of the steerable device may closely align with the user-instructed position.

An example in which the steerable device is unopposed is illustrated in FIG. 4. The positions of a given portion of the steerable device, also referred to as the slave positions, along the first direction of motion are represented by circles 404A and 404B. The movement of the steerable device in response to the user input is represented by the change in position from 404A to 404B. As can be seen, the position of the steerable device may closely track that of the proxy. In some embodiments, when moving in free space or substantially unopposed, the steerable device may move about 1:1 with the received user input, such as during process 352.

However, when used during a procedure, the steerable device may encounter an opposing force. For example, in a medical application where the steerable device is advanced through a passageway, the device may encounter resistance from the tissue that forms the passageway. Resistance may be fed back to the operator O in a number of ways. In some embodiments, opposing force may be translated into resistance, vibration, or other haptic feedback at the control device, and/or represented visually or by audio cue (e.g., at the display system 110).

An example in which the steerable device encounters an opposing force is illustrated in the control environment 500 of FIG. 5. User-instructed positions along the first direction of motion are represented by circles 502A and 502B, and the positions of the steerable device are represented by circles 504A and 504B. In the example, the first user input instructs the system to drive the steerable device such that a portion of the steerable device moves from user-instructed position 502A to user-instructed position 502B. However, due to an opposing force, additional force applied by the actuators may result in tension in the steering controls of the steerable device without corresponding movement in the steerable device. Accordingly, the steerable device might only move from 504A to 504B, which is less than the user-instructed movement from 502A to 502B. A position discrepancy may occur between the user-instructed position 502B and the corresponding position of the steerable device 504B as indicated by marker 506. This discrepancy may correspond to tension in the actuators and/or the steering controls of the steerable device, which may be referred to as wind-up. Some aspects of wind-up are beneficial, and the resulting tension may be used to guide the steerable device, to anchor the steerable device, and/or to manipulate a deformable passageway.

The discrepancy between the user-instructed position and the actual position may vary over time even without any input from the operator O. For example, while the user-instructed position might respond only to user instructions, the actual position of the steerable device may vary as the surrounding passageways move and apply three to the steerable device. An external force or load on the steerable device may change the actual position of the steerable device without changing the user-instructed position. In many of the examples that follow, the system may react based on the discrepancy between the user-instructed position and the actual position rather than the user input alone. For example, the system may apply an opposing force during a procedure to keep the steerable device in a fixed position relative to the surrounding anatomy even without being instructed by the operator O and without changing operating modes. From an operator's perspective, the system may hold the position of the steerable device seamlessly.

Referring to process 360 of FIG. 3, the system may determine the amount of discrepancy in the first direction between the position of the steerable device determined in process 358 and the user-instructed position of the user input received in process 352. As explained above, the discrepancy may vary based on changes in the user input and/or actual position of the elongate device due to external forces.

Subsequent user input, such as in the first direction, may further increase the discrepancy between the position of the steerable device and the user-instructed position. For example, the actuator force and the tension in the steerable device might increase in response to the user input and without significant movement of the steerable device. To avoid injury to the surrounding tissue, the system might only increase the tension and the corresponding discrepancy up to a predetermined threshold in response to the user input. The system may subsequently clip or ignore any additional user input in the first direction that would further move the user-instructed position and thereby increase the tension and/or discrepancy beyond the threshold. Suppressing the response of the steerable device beyond a threshold may protect the surrounding environment. The threshold may vary over the course of a procedure, and in some examples, the threshold may be reduced as the steerable device is moved deeper to reduce the risk of injury to increasingly narrow and/or delicate passageways.

When a user input is received to move the steerable device in an opposite direction, the tension may be decreased before the steerable device is driven in the opposite direction. Controlled adjustments to the wind-up may allow the operator O to set the tension appropriate to the task without moving the steerable device. Referring to process 362, the system may receive a second user input that instructs the system to move the steerable device in a second direction. In some examples, at least a portion of the instructed motion may be opposite the first direction. For example, the second direction may be directly opposite the first direction such as the second direction is left and the first direction is right, or the second direction is up and the first direction is down. As another example, the second direction may be partially opposite the first direction such as the second direction is east, and the first direction is northwest or southwest. As with the first user input, the second user input may be provided by an operator O using a control device of a master assembly 106, and the operator O may use the same control device to provide both the first user input and the second user input to the system. The receiving by the system may be performed substantially as described in process 352.

Referring to process 364 of FIG. 3 and to FIG. 6, the system may move the user-instructed position in response to the second user input and based on a catch-up profile. Examples of catch-up profiles are described in more detail below. For example, the catch-up profile may add a velocity to a velocity associated with the second user input. Referring to the control environment 600 of FIG. 6, the second user input may instruct the system to move the user-instructed position 602A to user-instructed position 602B. As can be seen, there is still some discrepancy 606 between the position of the steerable device 604, which might not change in response to the input, and the second user-instructed position 602B. However, the subsequent discrepancy 606 may be less than the previous discrepancy between the position of the steerable device 604 and the first user-instructed position 602A.

Based on the change in the discrepancy caused by process 364, the system may drive the steerable device to reduce the tension in the steerable device in response to the second user input based on the catch-up profile as illustrated by process 366. In some embodiments, the control system 112 of the medical system 100 may cause actuators of the manipulator assembly 102 to reduce the force applied to the steering controls of the steerable device corresponding to the first direction that was previously applied in response to the first user input. In some embodiments, the control system 112 may cause actuators that drive the instrument carriage 306 along the insertion stage 308 to reduce the force imparted on the steerable device corresponding to the first user input.

Referring to FIG. 6, the amount that the second user-instructed position 602B is moved in response to the second user input—and correspondingly, the amount that the tension is reduced may be determined in part by the catch-up profile. In an example where the second user input includes a measure of velocity, the amount that the user-instructed position is moved may be determined by applying any applicable velocity modification, such as a positional limit or a catch up modification from the catch-up profile. The modified velocity may then be integrated to determine the amount to move the user-instructed position. In some embodiments, the catch-up profile may provide a 1:1 relationship between an unwinding input (the user input that eliminates wind-up) and a winding input (the user input that generated the wind-up). For example, the magnitude or duration of user input that generates a given amount of discrepancy and/or tension in the steerable device may be about the same as the magnitude or duration of user input that eliminates that, amount of discrepancy and/or tension.

In some examples, the catch-up profile may be more sensitive to unwinding input than to winding input such that the input used to reduce the discrepancy and/or tension may be greater than the input used to generate the discrepancy and/or tension. In some examples, the catch-up profile may be less sensitive to unwinding input than to winding input such that the input used to reduce the discrepancy and/or tension may be less than the input used to generate the discrepancy and/or tension. The catch-up profile may include any combination of linear, non-linear, exponential, logarithmic, step, piece-wise, hyperbolic, parabolic, periodic/trigonometric, inverse hyperbolic, polynomial, modular, other monotonic functions, and/or the like that define the relationship between the reduction in discrepancy and/or tension and an aspect of the user input.

In some examples, the catch-up profile may be such that the position discrepancy and tension are more sensitive to user inputs that reduce tension than to user inputs that increase tension. For example, the slope of the unwinding function may be greater than the slope of the winding function. This increased sensitivity to unwinding input may make the system feel more responsive.

In some examples, the catch-up profile may include two or more regions of varying slopes. In these examples, the slope may be proportional to the discrepancy, and the regions of greater discrepancy may have greater slope and may be more sensitive to unwinding user input than regions with less discrepancy. Reducing the sensitivity when the discrepancy is smaller may reduce the tendency to overshoot the neutral position or accidentally begin moving the steerable device in an opposite direction.

In some examples, the catch-up profile for reducing discrepancy may include two regions. In a first region where the discrepancy is greater, the user input may be more likely to represent an intent to fine-tune the wind-up, and the profile may be relatively less sensitive to user input to allow the operator O to make precise adjustments to the tension. In a second region where the discrepancy is less, the user input may be more likely to represent an intent to move the steerable device in the second direction. Accordingly, the profile may be relatively more sensitive to user input in the second region to make the system more responsive.

The particular catch-up profile and aspects of the catch-up profile such as the function(s), slope(s), sensitivities, and other aspects may depend on 1) an amount of discrepancy (e.g., position error); 2) any aspect of the user input—such as the magnitude of the input, the duration of the input, an interval length between inputs, and/or other suitable aspect; 3) time; 4) movement of the steerable device due to external loads; 5) smoothness of the response of the actuator or other tensioning mechanism; 6) a shape of the steerable device; 7) a sensitivity of the tissue that makes up the passageway; 8) curvature of the anatomy; 9) an operator preference, and/or 10) other suitable aspects of the system, the operator O, or the procedure.

In some examples, the catch-up profile may provide a decaying exponential where the user-instructed position approaches the device position asymptotically when there is no (or little) movement of the steerable device due to external loads, the user input is at a constant rate, and the catch-up term is a linear function of the instantaneous positional error. For some systems and actuator configurations, the decaying exponential may provide a smooth change in tension in the steerable device.

Referring to process 368 of FIG. 3, the system may receive a third user input that further instructs the system to move the steerable device in the second direction of motion, such as after the user-instructed position and the position of the steerable device have converged. The third user input may be provided by an operator O using a control device of a master assembly 106, and the operator O may use the same control device to provide the first user input, the second user input, and the third user input to the system. The receiving by the system may be performed substantially as described in process 352.

Referring to process 370, the system may move the user-instructed position in response to the third user input. As the position discrepancy has been eliminated, referring to process 372, the system may control the steerable device to move in the second direction of movement in response to the third user input. This may be performed substantially as described in process 356.

During a medical procedure, the method 350 may be repeated as the steerable device traverses a patient anatomy. For example, a steerable device traversing a branched anatomic area, such as a human lung, may be inserted into and removed from a series of anatomic branches using the method 350 to manage tension forces associated with discrepancies between the user-instructed positions and the corresponding positions of the steerable device.

Figure 7:
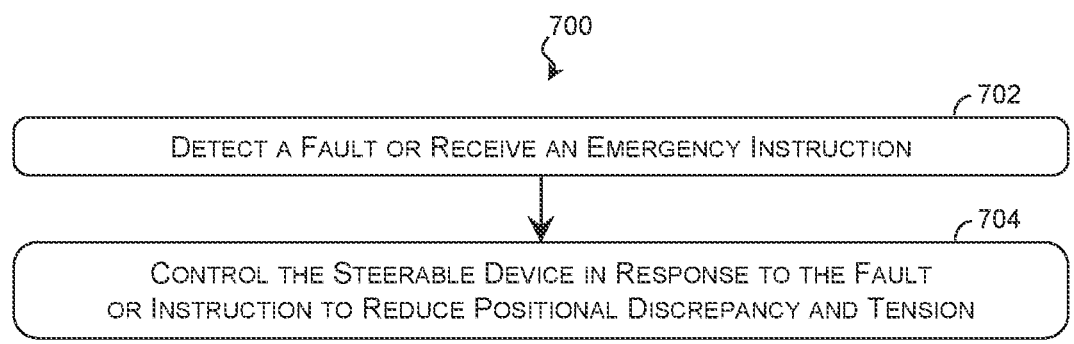
FIG. 7 is a flowchart illustrating a method of controlling a steerable device in response to a fault according to some embodiments.

At any time, the system may detect a fault in the system, the steerable member, and/or the procedure. Based on detecting the fault, the system may eliminate the discrepancy and the tension in the steerable member if any exist. FIG. 7 is a flowchart describing a method 700 of controlling a steerable device in response to a fault according to some embodiments. The method 700 is illustrated in FIG. 7 as a set of operations or processes. One or more of the illustrated processes might not be performed in some embodiments of method 700. Additionally, one or more processes that are not expressly illustrated in FIG. 7 may be included before, after, in between, or as part of the illustrated processes. In some embodiments, one or more of the processes of method 700 may be implemented, at least in part, in the form of executable code stored on non-transitory, tangible, machine-readable media that, when run by one or more processors (e.g., the processors of the control system 112 above), may cause the one or more processors to perform one or more of the processes. The method 700 may be performed at any time including during method 350, described above.

Referring to process 702 of FIG. 7, a system, such as the medical system 100 above, may detect a fault in the system, the steerable member, and/or the procedure or may receive an emergency instruction from the operator O. Referring to process 704 of FIG. 7, if a position discrepancy exists, the system may control the steerable device to reduce the position discrepancy in response to the fault or emergency instruction. The rate and degree to which the position discrepancy is reduced may be similar to the catch-up profile in that it may include any combination of linear, non-linear, exponential, logarithmic, step, piece-wise, hyperbolic, parabolic, periodic/trigonometric, inverse hyperbolic, polynomial, modular, other monotonic functions, and/or the like to determine the rate and degree of reducing position discrepancy and tension in the steerable device. Aspects of this behavior, such as the function(s), slope(s), and other aspects, may depend on a shape of the elongate device, a sensitivity of the tissue that makes up the passageway, curvature of the anatomy, an operator preference, or other suitable aspects of the system, the operator O, or the procedure. The rate and degree to which the position discrepancy is reduced may be selected so that there is no inadvertent movement of the steerable device that is perceptible to the operator O.

In some examples, the position discrepancy may be immediately eliminated, and the tension in the steerable device may be immediately released. Rapid reduction in tension may be beneficial in delicate environments to reduce the risk of damage or injury caused by the steerable device. In some examples, the position discrepancy may be reduced at a slower rate to avoid elastic rebound, buckling or bunching of the steering controls, or other effects of the actuators or steering controls.

Various Examples of Implementations of the Disclosure

This disclosure describes various instruments and portions of instruments in terms of their state in three-dimensional space. For example, the term position refers to the location of an object or a portion of an object in a three-dimensional space (e.g., three degrees of translational freedom along Cartesian x-, y-, and z-coordinates). The term orientation refers to the rotational placement of an object or a portion of an object (e.g., one or more degrees of rotational freedom, such as roll, pitch, and yaw). The term pose refers to the position of an object or a portion of an object in at least one degree of translational freedom and to the orientation of that object or portion of the object in at least one degree of rotational freedom (e.g., up to six total degrees of freedom). The term shape refers to a set of poses, positions, or orientations measured along an object.

One or more elements in embodiments of this disclosure may be implemented in software to execute on a processor of a computer system such as control processing system. When implemented in software, the elements of the embodiments of this disclosure may be code segments to perform various tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and/or magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In some examples, the control system may support wireless communication protocols such as Bluetooth, Infrared Data Association (IrDA), HomeRF, IEEE 802.11, Digital Enhanced Cordless Telecommunications (DET), ultra-wideband (UWB), ZigBee, and Wireless Telemetry.

Medical tools may be delivered through the flexible elongate devices (e.g., catheters) disclosed herein and may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. Medical tools may include image capture probes that include a stereoscopic or monoscopic camera for capturing images (including video images). Medical tools may additionally house cables, linkages, or other actuation controls that extend between its proximal and distal portions to controllably bend the distal portion of a medical tool. Steerable instruments are described in detail in U.S. Pat. No. 7,316,681 (filed on Oct. 4, 2005 and titled "Articulated Surgical Instrument for Performing Minimally Invasive Surgery with Enhanced Dexterity and Sensitivity") and U.S. patent application Ser. No. 12/286,644 (filed Sep. 30, 2008 and titled "Passive Preload and Capstan Drive for Surgical Instruments"), which are incorporated by reference herein in their entireties.

The systems described herein may be suited for navigation and treatment of anatomic tissues, via natural or surgically created passageways, in any of a variety of anatomic systems, including the lung, colon, intestines, kidneys and kidney calices, brain, heart, circulatory system including vasculature, and/or the like.

Note that the processes and displays presented might not inherently be related to any particular computer or other apparatus. Various general-purpose systems may be used with programs in accordance with the teachings herein, or it may prove convenient to construct a more specialized apparatus to perform the operations described. In addition, it will be appreciated that a variety of programming languages may be used to implement the examples described herein.

While certain examples have been described and shown in the accompanying drawings, it is to be understood that such examples are merely illustrative of and are not restrictive, and that the described examples are not limited to the specific constructions and arrangements shown and described, since various other modifications may occur to those ordinarily skilled in the art.

What is claimed is:

1. A system comprising:
a control device configured to receive user inputs;
a manipulator system including an actuator configured to receive and drive a steerable device; and
a control system communicatively coupled to the manipulator system and the control device, the control system configured to:
track a virtual user-instructed position based on a first user input;
determine a device position of a portion of the steerable device;
determine a position discrepancy in a first direction between the determined device position and the virtual user-instructed position;
receive a second user input commanding motion of the steerable device in a second direction, wherein at least a portion of the second direction is opposite the first direction; and
in response to the second user input, reduce the position discrepancy based on an aspect of the second user input and a catch-up profile.

2. The system of claim 1, wherein the control system is configured to reduce the position discrepancy by reducing tension in a steering control of the steerable device.

3. The system of claim 1, wherein the aspect of the second user input comprises at least one of a magnitude of the second user input or a duration of the second user input.

4. The system of claim 1, wherein the catch-up profile is based on at least one of: a shape of the steerable device, a sensitivity of a passageway in which the steerable device is disposed, or an operator preference.

5. The system of claim 1, wherein the catch-up profile reduces the position discrepancy by applying a catch-up velocity to the second user input.

6. The system of claim 5, wherein the catch-up velocity is configured such that control of the steerable device is more sensitive to input that reduces the position discrepancy than to input that increases the position discrepancy.

7. The system of claim 1, wherein the catch-up profile includes a first region configured to have a first sensitivity and a second region configured to have a second sensitivity that is different from the first sensitivity.

8. The system of claim 7, wherein the first region is associated with a greater position discrepancy than the second region, and the first sensitivity is greater than the second sensitivity.

9. The system of claim 7, wherein the first region is associated with a greater position discrepancy than the second region, and the first sensitivity is less than the second sensitivity.

10. The system of claim 1, wherein the control system is configured to:
receive a third user input commanding motion of the steerable device in the first direction;
determine that the third user input causes the position discrepancy to exceed a threshold; and
suppress a response to the third user input based on the determination that the third user input causes the position discrepancy to exceed the threshold.

11. The system of claim 1, wherein the virtual user-instructed position does not change in response to a load on the steerable device.

12. The system of claim 1, wherein the control system is configured to:
detect a fault; and
in response to the fault, reduce the position discrepancy without motion of the steerable device that is perceptible to an operator.

13. The system of claim 12, wherein the control system is configured to reduce the position discrepancy in response to the fault by eliminating tension in a steering control of the steerable device.

14. An apparatus comprising:
one or more processors; and
non-transitory computer memory storing machine-executable instructions that, when executed by the one or more processors, cause the apparatus to:
receive, from a control device, a first user input commanding motion of a steerable device in a first direction;
track a virtual user-instructed position based on the first user input;
command an actuator coupled to the steerable device to move the steerable device in the first direction based on the first user input, wherein movement of the steerable device in response to the first user input generates a position discrepancy;
detect, from a sensor of the steerable device, a device position of a portion of the steerable device;
determine a measure of the position discrepancy;
receive, from the control device, a second user input commanding motion of the steerable device in a second direction, wherein at least a portion of the second direction is opposite the first direction; and
in response to the second user input, reduce the position discrepancy based on an aspect of the second user input and a catch-up profile.

15. The apparatus of claim 14, wherein the position discrepancy is associated with a tension in the steerable device, and wherein the non-transitory computer memory stores machine-executable instructions that, when executed by the one or more processors, cause the apparatus to command the actuator to reduce the tension in the steerable device based on the catch-up profile.

16. The apparatus of claim 14, wherein the aspect of the second user input includes at least one of a magnitude of the second user input or a duration of the second user input.

17. The apparatus of claim 14, wherein the catch-up profile is based on at least one of: a shape of the steerable device, a sensitivity of a passageway in which the steerable device is disposed, or an operator preference.

18. The apparatus of claim 14, wherein the catch-up profile applies a catch-up velocity to the second user input.

19. The apparatus of claim 14, wherein the catch-up profile is such that the apparatus is more sensitive to user input that reduces the position discrepancy than to user input that increases the position discrepancy.

20. The apparatus of claim 14, wherein the catch-up profile has a first region associated with greater position discrepancy and a second region associated with lesser position discrepancy, and wherein a first sensitivity of the first region is greater than a second sensitivity of the second region.

* * * * *